United States Patent
Miljanić et al.

(10) Patent No.: US 9,475,777 B2
(45) Date of Patent: Oct. 25, 2016

(54) THERMALLY ROBUST, HIGHLY POROUS, AND PARTIALLY FLUORINATED ORGANIC FRAMEWORK WITH AFFINITY FOR HYDROCARBONS, FLUOROCARBONS AND FREONS

(71) Applicant: UNIVERSITY OF HOUSTON SYSTEM, Houston, TX (US)

(72) Inventors: Ognjen Š Miljanić, Houston, TX (US); Teng-Hao Chen, Houston, TX (US); Ilya Popov, Houston, TX (US); Watchareeya Kaveevivitchai, Houston, TX (US); Olafs Daugulis, Houston, TX (US)

(73) Assignee: UNIVERSITY OF HOUSTON SYSTEM, Houston, TX (US)

(*) Notice: Subject to any disclaimer, the term of this patent is extended or adjusted under 35 U.S.C. 154(b) by 0 days.

(21) Appl. No.: 14/707,812

(22) Filed: May 8, 2015

(65) Prior Publication Data

US 2015/0329492 A1    Nov. 19, 2015

Related U.S. Application Data

(60) Provisional application No. 61/994,482, filed on May 16, 2014.

(51) Int. Cl.
*C07D 231/12* (2006.01)
*B01J 20/22* (2006.01)

(52) U.S. Cl.
CPC ............ *C07D 231/12* (2013.01); *B01J 20/226* (2013.01)

(58) Field of Classification Search
None
See application file for complete search history.

(56) References Cited

U.S. PATENT DOCUMENTS 8,993,806 B2 *   3/2015   Zhang ................... B01D 53/02
                                                564/305

* cited by examiner

*Primary Examiner* — Kamal Saeed
(74) *Attorney, Agent, or Firm* — Conley Rose, P.C.

(57) ABSTRACT

Porous partially fluorinated materials which bind aliphatic and aromatic hydrocarbons, fluorocarbons and freons with high weight adsorption capacities are provided. Such compounds may be used in separation of materials by exclusion such as selective separation of isomers of xylene.

15 Claims, 5 Drawing Sheets

THERMALLY ROBUST, HIGHLY POROUS, AND PARTIALLY FLUORINATED ORGANIC FRAMEWORK WITH AFFINITY FOR HYDROCARBONS, FLUOROCARBONS AND FREONS

CROSS-REFERENCE TO RELATED APPLICATIONS

This application claims priority to U.S. Provisional application 61/994,482 filed May 16, 2014 and is incorporated herein in its entirety.

STATEMENT REGARDING FEDERALLY SPONSORED RESEARCH OR DEVELOPMENT

This invention was made with government support under Grant No. CHE-1151292 awarded by the National Science Foundation. The United States government has certain rights in the invention.

BACKGROUND

1. Field of the Disclosure

This disclosure generally relates to a new class of partially fluorinated porous materials which bind aliphatic and aromatic hydrocarbons, fluorocarbons and freons with high weight adsorption capacities. More particularly, the disclosure relates to separation of materials by exclusion principle, as well as by differential diffusion rates, and selective separation of isomers of xylene by the same principle.

2. Background of the Technology

Traditional Metal-Organic Frameworks (MOFs) and Covalent Organic Frameworks (COFs) are porous materials characterized by thermal stability, high porosities and modular synthesis. Despite these advantages, their applications are hampered by limited solubility, prohibitively high melting and sublimation points, and moisture sensitivity.

Chemistry of such porous materials has been advanced over the past two decades with the development of crystallographically ordered hybrid structures such as MOFs[1] and COFs.[2,3] These two classes of materials allow facile modification of pore sizes, shapes, surface functionalities and polarities. In three-dimensional MOFs and COFs, pores are generally formed by surrounding them on all sides with covalent bonds: thus, the whole crystal is one molecule, and the well-defined atomic positions translate into well-defined pores.

While "crystal-as-a-molecule" strategy allows superior control over pore properties, MOFs and COFs are difficult to recrystallize, difficult to grow on surfaces[4] or deposit from solution,[5] and their characterization is overly dependent on the growth of crystalline samples. In addition, many of the metal-ligand bonds in MOFs and reversibly formed organic bonds in COFs (e.g. boroxines, boronate esters, imines) are hydrolytically highly sensitive.

Formation of pores within a crystal structure should not require that the entire crystal be an infinite covalently connected net, and should simply require a crystal of a molecule which organizes into a porous structure. However, such structures are rare and difficult to predict a priori;[6] furthermore, even when a small molecule can be organized into a porous structure, such structures are typically fragile after solvent removal and they are unsuitable for many applications.

Recently, molecular crystals characterized by high porosity have been developed.[7-18] These can be intrinsically or extrinsically porous. In the intrinsically porous case, the molecule itself contains a large pore, typically within a macrocycle or a molecular capsule. Organization of these within the crystal then results in an extended structure which replicates individual molecules' porosities. In extrinsically porous case, the molecule itself is inherently porous, and all porosity comes as the consequence of its crystal packing. Using an intrinsic strategy, materials with surface areas over 3,500 m$^2$ g$^{-1}$ have been constructed, as well as extrinsically porous molecular crystals with surface areas in excess of 3,000 m$^2$ g$^{-1}$. However, these molecular crystals use hydrolytically sensitive imine and boronate ester functionalities and therefore are fragile.

Therefore, there is a need for lightweight, solution processable materials that are easily synthesized, thermally stable, and highly porous, wherein such materials bind aliphatic and aromatic (such as xylenes) hydrocarbons, fluorocarbons, and freons with high weight adsorption capacities while being hydrolytically stable and non-fragile. Such materials would serve an unmet need in petrochemical industry, environmental remediation and analysis, and pre- and post-combustion technologies.

BRIEF SUMMARY OF THE DISCLOSURE

Herein disclosed are non-covalent organic frameworks (nCOF) comprising in some embodiments a small organic molecule whose crystal structure contains large and empty pores. In some embodiments, such a structure is held together by a combination of [N—H . . . N] hydrogen bonds between its terminal pyrazole rings and [π . . . π] stacking between the electron-rich pyrazoles and electron-poor tetrafluorobenzenes. In some embodiments, such as synergistic arrangement makes these structures stable to at least 250° C. In further embodiments, their internal pores have accessible Brunauer-Emmett-Teller (BET) surface area of 1,159 m$^2$ g$^{-1}$. Crystals of these nCOF adsorb hydrocarbons, Freons and fluorocarbons, the latter two being both ozone-depleting substances and potent greenhouse gases with weight capacities of up to 75% (defined as weight of the adsorbed analyte divided by weight of the nCOF material, and multiplied by 100%). In some embodiments, such structures are soluble, lightweight (since they do not have metals), and completely indifferent to moisture.

One embodiment of a non-covalent organic framework comprises a compound of:

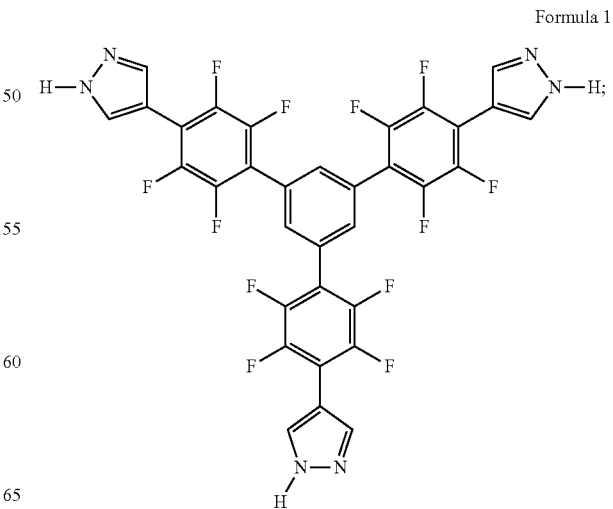

Formula 1 wherein the compound forms a porous supramolecular structure; in another embodiment the non-covalent organic framework comprising the compound of Formula 1, comprises at least one polymorph of the compound of Formula 1; in a further embodiment a non-covalent organic framework comprising the compound of Formula 1 (also designated as compound [1]) comprises a mixture of polymorphs. In another embodiment, said polymorphs are detectable by X-ray powder diffraction.

In some embodiments described herein, a compound of Formula 1 forms a porous supramolecular structure. In another embodiment of the non-covalent framework herein described, the framework is comprised of a unit cell as disclosed in Table 2. In another embodiment herein described, the non-covalent framework comprised of compound 1, further comprises fluorine lined channels, wherein said channels are about 5 to about 30 Angstroms in diameter; about 10 to about 20 Angstroms in diameter; 15 to about 18 Angstroms in diameter; and about 16.5 Angstroms in diameter.

In another embodiment of the non-covalent framework of compound 1, the framework comprises a weight adsorption capacity of about 95% for analytes; in another embodiment the framework comprises a weight adsorption capacity of about 90% for analytes; the framework comprises a weight adsorption capacity of about 85% for analytes; the framework comprises a weight adsorption capacity of about 75% for analytes; and a weight adsorption capacity of about 60% for analytes. In another embodiment, the analytes comprise aliphatic hydrocarbons, aromatic hydrocarbons, fluorocarbons; and freons.

In another embodiment described herein, the non-covalent framework comprising the compound of Formula 1 differentially binds ortho-xylene; meta-xylene and para-xylene; in another embodiment the non-covalent framework differentially binds ortho-xylene by at least 20 weight %, in a further embodiment the non-covalent framework differentially binds meta-xylene by at least 20 weight %; and in a still further environment the non-covalent framework differentially binds para-xylene at less than 10 weight %. In another embodiment herein described, the non-covalent framework comprising of a compound of Formula 1 is thermally stable, in a further embodiment the framework is hydrolytically stable, and in a further still embodiment the non-covalent framework of a compound of Formula 1 adsorbs $N_2$, $O_2$ and $CO_2$.

In another embodiment, a non-covalent organic framework is disclosed that comprises a core structure comprising a 5, 6, or 7 membered aromatic ring structure, wherein said core is selectively substituted with alternating electron rich and election deficient groups, which may be interspersed with further substituents, wherein said substituents may be organic or inorganic, but maintaining the alternating pattern of electron rich . . . electron deficient. In other embodiments, a non-covalent organic framework is disclosed that comprises a central ring or core, wherein the central ring is selected from a group comprising: 1, 2, 3, 4, 5, 6-hexasubstituted benzene; a 1, 2, 4, 5-tetrasubstituted benzene; a 1,3,5-trisubstituted or a 1,4-disubstituted benzene; wherein any of positions 1, 2, 3, 4, 5, and 6 may be substituted or unsubstituted, wherein, when said groups are substituted they comprise of alternating electron poor (deficient) and electron rich substituent groups (or rings), wherein said electron-poor groups or rings comprise tetra, tri or di fluorobenzenes, oligocyanobenzenes, and wherein an electron-rich group of ring comprises: benzene, pirydone, triazole, pyrazole, pyridine, and substituted benzenes.

DETAILED DESCRIPTION OF THE DISCLOSED EMBODIMENTS

Figure 1:
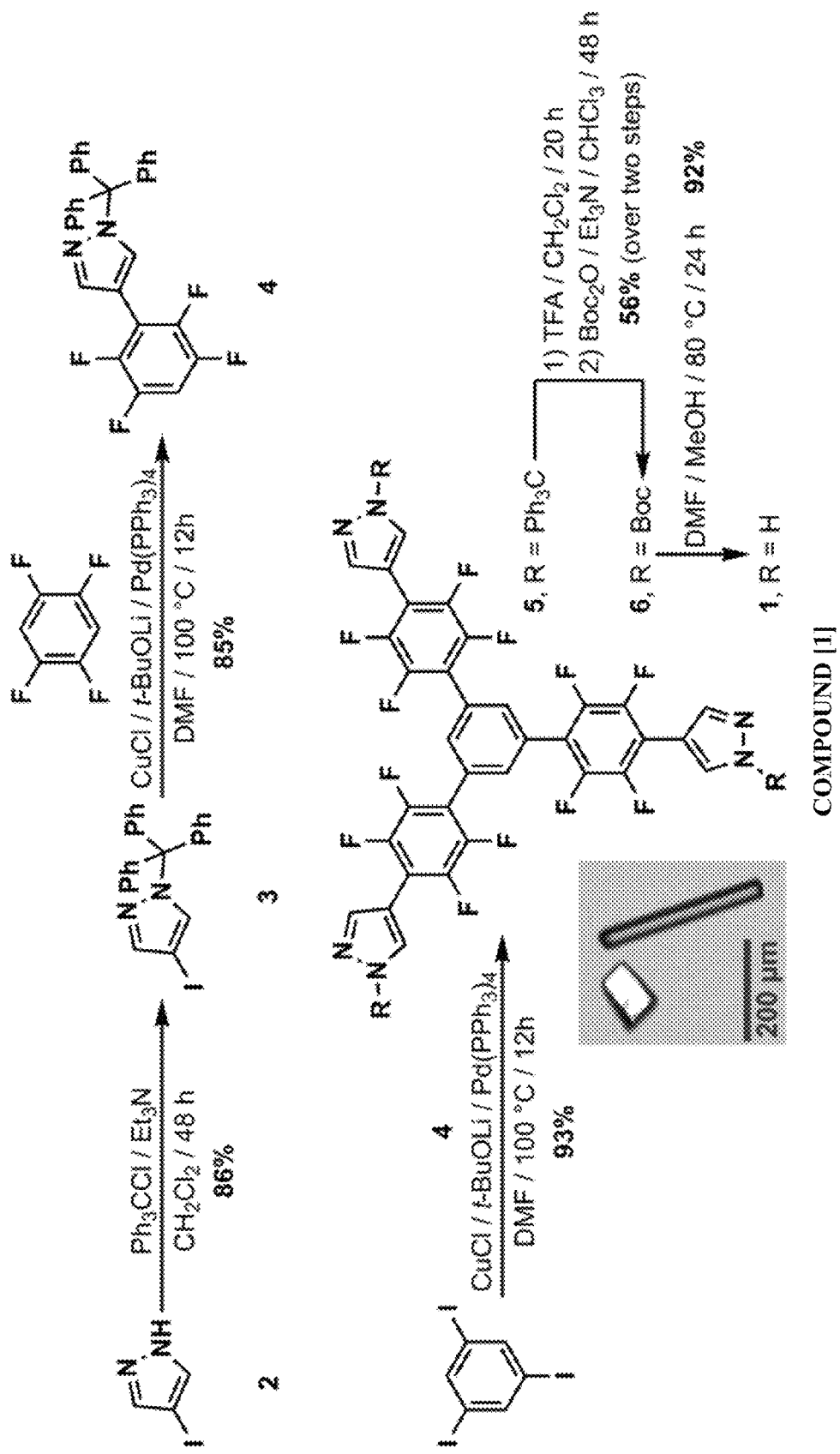
FIG. 1: is a schematic depicting the synthesis of compound [1]: the reaction of 4-iodopyrazole 2 with trityl chloride produces protected pyrazole 3, which is then coupled to 1,2,4,5-tetrafluorobenzene to give 4. Threefold coupling of 4 with 1,3,5-triiodobenzene generates trigonal precursor 5. A series of protecting group manipulations produces 1. The insert shows an image of typical crystals of 1 in accordance with an embodiment of this invention.

Disclosed herein is the synthesis of a trispyrazole 1 (FIG. 1) which, in some embodiments, organizes into a highly robust supramolecular structure with extrinsic high porosity through a combination of [π . . . π] stacking[8] and hydrogen bonding therefore forming a nCOF. In some embodiments, it is highly porous and has a high gas binding ability. In addition, Compound 1 also captures, in some embodiments, three quarters of its own weight in hydrocarbon and fluorocarbon analytes, which is a characteristic of interest both in fuel processing and the capture of potent greenhouse gases.

In one embodiment, these molecular materials are constructed from a central core which may have linear, trigonal, tetragonal or hexagonal geometry and 2-6 radially projecting arms which comprise fluorinated and electron-rich groups in an alternating arrangement, the resultant Pi-Pi stacking between electron-rich and electron-poor nuclei in these arms creates the porous structure. These materials can bind many fluorophilic and nonpolar guests (molecules). Significantly, they quickly bind ortho- and meta-xylenes at least about 20 weight % (at least 20% of the weight of the molecule is comprised from the presence of xylene held adsorbed within the pores of the trispyrazole), while they bind para xylene much slower and to a lower weight percentage. In some embodiments, as these materials show low and slow adsorption of para-xylene, the separation of isomers of xylene is based on exclusion principles as well as differential rates of diffusion through the material.

TABLE 1

Sorption capacities and other characteristics of guest adsorbed within the pores of compounds 1.

| Guest species | Boiling point [° C.] | 20-Year greenhouse gas potential (vs. CO$_2$) | Adsorption in 1 | | Desorption temperature [° C.] |
|---|---|---|---|---|---|
| | | | Weight %$^a$ | In moles, per mole of 1$^b$ | |
| Toluene | 110 | — | 30.6 (29.7) | 2.39 | 62 |
| Hexane | 68 | — | 27.7 (27.4) | 2.31 | 52 |
| Cyclohexane | 81 | — | 25.7 (25.6) | 2.20 | 61 |
| Chloroform | 61 | — | 52.5 (53.4) | 3.17 | 62 |
| Dichloromethane | 40 | 31 | 49.8 (49.6) | 4.22 | 45 |
| Perfluorohexane | 56 | 6,600 | 74.0 (73.6) | 1.58 | 62 |
| CFC-113 (Cl$_2$FC—CClF$_2$) | 48 | 6,540 | 65.6 (64.9) | 2.52 | 62 |
| HCFC-225ca (CF$_3$CHF$_2$CHCl$_2$) | 51 | 429 | 58.0 (58.0) | 2.06 | 63 |

$^a$Values in parenthesis indicate weight adsorption capacities observed in the second attempt.
$^b$Molar values were calculated using weight adsorption data from the first attempt.

Xylenes are a major petrochemical component that contributes to 0.5-1% of crude oil by weight. Among them, the most valuable is para-xylene, but its separation from the ortho- and meta-isomers is currently challenging since their boiling points are close. Current industrial process uses a zeolite-based DSM-5 material to interconvert the xylenes and then separate based on their relative rates of diffusion through the material. The para-xylene passes through the material at the highest rate. However in embodiments of the nCOF separation material herein disclosed (such as compound 1), para-xylene is selectively blocked from the pores as described above, resulting in a selective uptake of ortho- and meta-xylenes. This demonstrates a novel and useful method for xylene separation.

Further xylene isomers are also used as starting materials for many industrial polymers, therefore finding materials which can selectively isolate para-xylene (the most valuable of the three isomers) is of industrial value (see for example U.S. Pat. No. 5,441,608; U.S. Pat. No. 5,849,981; U.S. Pat. No. 2,672,487; and U.S. Pat. No. 4,864,069, incorporated herein in their entirety by reference).

In some embodiments the nCOF materials described herein may be further modified while maintaining their porosity, high adsorption capacities and selectivities in the separation of "guests/molecules" of interest. Specifically, the pyrazole ring may be switched for other moieties that provide the desirable Pi-Pi stacking, such as but not limited to: benzene, triazole, and pyridine, and also switched with other such moieties that may allow the dissection or amplification of hydrogen bonding and [π . . . π] stacking effects.

In some embodiments, nCOFs may be constructed that are linear and tetragonal versions of the prepared fluorinated molecules that also have similar adsorption capacities and selectivities. Other embodiments may include the pre or post synthetic replacement of fluorine groups with other nucleophile species, and other embodiments may test the effects of varying the conformation of the arms of compound 1 which may yield an isoreticular series of more porous structures.

The synthesis of compound 1 commenced with the commercially available 4-iodopyrazole (2 in FIG. 1). The masking of its N—H bond with a trityl (Ph$_3$C—) group gave compound 3, which was subjected to a palladium-catalyzed coupling with an excess of 1,2,4,5-tetrafluorobenzene to produce intermediate 4. In 4, only one of the two C—H bonds of tetrafluorobenzene was replaced with a functionalized pyrazole moiety. Another palladium-catalyzed coupling followed, combining 3.3 equivalents of 4 with 1,3,5-triiodobenzene and resulting in the trigonal precursor 5. The trityl groups in 5 were removed by acidic treatment, and subsequently replaced with tert-butoxycarbonyl (Boc) group. Heating of a solution of 6 in DMF and MeOH for one day at 80° C. resulted in single crystals of compound 1. This protocol utilized previously reported protocols for the in situ deprotection of Boc group[9] and concurrent binding to metals.[10,11]

Single-crystal X-ray diffraction data on 1 (Table 2) was achieved with synchrotron radiation.

TABLE 2

Compound [1] of Formula 1: Crystal Structure Unit Cell Data

```
data_squeeze
_audit_creation_method               SHELXL-97
_chemical_name_systematic
_chemical_formula_sum
 'C33 H12 F12 N6'
_chemical_formula_weight             720.49
loop_
_atom_type_symbol
_atom_type_description
_atom_type_scat_dispersion_real
_atom_type_scat_dispersion_imag
_atom_type_scat_source
 'C'  'C'   -0.0001  0.0005
 'International Tables Vol C Tables 4.2.6.8 and 6.1.1.4'
 'H'  'H'    0.0000  0.0000
 'International Tables Vol C Tables 4.2.6.8 and 6.1.1.4'
 'N'  'N'    0.0005  0.0010
 'International Tables Vol C Tables 4.2.6.8 and 6.1.1.4'
 'F'  'F'    0.0038  0.0031
```

TABLE 2-continued

Compound [1] of Formula 1: Crystal Structure Unit Cell Data

| | |
|---|---|
| 'International Tables Vol C Tables 4.2.6.8 and 6.1.1.4' | |
| _symmetry_cell_setting | Monoclinic |
| _symmetry_space_group_name_H-M | C2/c |
| loop_ | |
| _symmetry_equiv_pos_as_xyz | |
| 'x, y, z' | |
| '−x, y, −z+½' | |
| 'x+½, y+½, z' | |
| '−x+½, y+½, −z+½' | |
| '−x, −y, −z' | |
| 'x, −y, z−½' | |
| '−x+½, −y+½, −z' | |
| 'x+½, −y+½, z−½' | |
| _cell_length_a | 19.314(9) |
| _cell_length_b | 34.639(16) |
| _cell_length_c | 22.045(10) |
| _cell_angle_alpha | 90.00 |
| _cell_angle_beta | 113.164(4) |
| _cell_angle_gamma | 90.00 |
| _cell_volume | 13560(11) |
| _cell_formula_units_Z | 12 |
| _cell_measurement_temperature | 100(2) |
| _exptl_crystal_density_diffrn | 1.059 |
| _exptl_crystal_density_method | 'not measured' |
| _exptl_crystal_F_000 | 4320 |
| _exptl_absorpt_coefficient_mu | 0.013 |
| _exptl_absorpt_process_details | sadabs |
| _exptl_special_details: | |
| _diffrn_ambient_temperature | 100(2) |
| _diffrn_radiation_wavelength | 0.41328 |
| _diffrn_radiation_source | 'fine-focus sealed tube' |
| _diffrn_radiation_monochromator | graphite |
| _diffrn_reflns_number | 31825 |
| _diffrn_reflns_av_R_equivalents | 0.0604 |
| _diffrn_reflns_av_sigmaI/netI | 0.1362 |
| _diffrn_reflns_limit_h_min | −11 |
| _diffrn_reflns_limit_h_max | 21 |
| _diffrn_reflns_limit_k_min | −40 |
| _diffrn_reflns_limit_k_max | 32 |
| _diffrn_reflns_limit_l_min | −25 |
| _diffrn_reflns_limit_l_max | 21 |
| _diffrn_reflns_theta_min | 0.68 |
| _diffrn_reflns_theta_max | 13.96 |
| _reflns_number_total | 10079 |
| _reflns_number_gt | 3108 |
| _reflns_threshold_expression | >2sigma(I) |
| _computing_structure_solution | 'SHELXS-97 (Sheldrick, 2008)' |
| _computing_structure_refinement | 'SHELXL-97 (Sheldrick, 2008)' |
| _computing_molecular_graphics | 'Bruker SHELXTL' |
| _computing_publication_material | 'Bruker SHELXTL' |
| _refine_special_details | |
| ; | |
| Refinement of $F^2$ against ALL reflections. The weighted R-factor wR and goodness of fit S are based on $F^2$, conventional R-factors R are based on F, with F set to zero for negative $F^2$. The threshold expression of $F^2 > 2\mathrm{sigma}(F^2)$ is used only for calculating R-factors(gt) etc. and is not relevant to the choice of reflections for refinement. R-factors based on $F^2$ are statistically about twice as large as those based on F, and R-factors based on ALL data will be even larger. | |
| ; | |
| _refine_ls_structure_factor_coef | Fsqd |
| _refine_ls_matrix_type | full |
| _refine_ls_weighting_scheme | calc |
| _refine_ls_weighting_details | |
| 'calc w=1/[\s 2 (Fo 2)+(0.2000P) 2+0.0000P] where P=(Fo 2+2Fc 2)/3' | |
| _atom_sites_solution_primary | direct |
| _atom_sites_solution_secondary | difmap |
| _atom_sites_solution_hydrogens | geom |
| _refine_ls_hydrogen_treatment | mixed |
| _refine_ls_extinction_method | SHELXL |
| _refine_ls_extinction_coef | 0.015(2) |
| _refine_ls_extinction_expression | |
| 'Fc*=kFc[1+0.001xFc 2 \l 3/sin(2\q)]^-¼' | |
| _refine_ls_number_reflns | 10079 |
| _refine_ls_number_parameters | 645 |
| _refine_ls_number_restraints | 353 |
| _refine_ls_R_factor_all | 0.2510 |
| _refine_ls_R_factor_gt | 0.1572 |
| _refine_ls_wR_factor_ref | 0.4912 |
| _refine_ls_wR_factor_gt | 0.4553 |
| _refine_ls_goodness_of_fit_ref | 1.261 |
| _refine_ls_restrained_S_all | 1.247 |
| _refine_ls_shift/su_max | 0.049 |
| _refine_ls_shift/su_mean | 0.007 |
| loop_ | |
| _atom_site_label | |
| _atom_site_type_symbol | |
| _atom_site_fract_x | |
| _atom_site_fract_y | |
| _atom_site_fract_z | |
| _atom_site_U_iso_or_equiv | |
| _atom_site_adp_type | |
| _atom_site_occupancy | |
| _atom_site_symmetry_multiplicity | |
| _atom_site_calc_flag | |
| _atom_site_refinement_flags | |
| _atom_site_disorder_assembly | |
| _atom_site_disorder_group | |

C1 C 0.9348(5) 0.5499(2) 0.2193(4) 0.0541(16) Uani 1 1 d U . .
H101 H 0.8843 0.5417 0.1959 0.065 Uiso 1 1 calc R . .
C2 C 1.0000 0.5263(3) 0.2500 0.0532(16) Uani 1 2 d SU . .
C3 C 1.0000 0.4828(3) 0.2500 0.0370(13) Uani 1 2 d SU . .
C4 C 0.9373(4) 0.4610(2) 0.2105(4) 0.0367(12) Uani 1 1 d U . .
C5 C 0.9377(4) 0.42153(19) 0.2098(4) 0.0369(12) Uani 1 1 d U . .
C6 C 1.0000 0.3994(3) 0.2500 0.0365(13) Uani 1 2 d SU . .
C7 C 1.0000 0.3563(3) 0.2500 0.0399(14) Uani 1 2 d SU . .
C8 C 0.9409(4) 0.33594(18) 0.2567(4) 0.0397(13) Uani 1 1 d U . .
H108 H 0.9005 0.3499 0.2605 0.048 Uiso 1 1 calc R . .
C9 C 0.9394(4) 0.29579(19) 0.2578(4) 0.0403(13) Uani 1 1 d U . .
C10 C 1.0000 0.2760(3) 0.2500 0.0402(14) Uani 1 2 d SU . .
H110 H 1.0000 0.2486 0.2500 0.048 Uiso 1 2 calc SR . .
C11 C 0.8777(4) 0.27368(18) 0.2615(4) 0.0367(10) Uani 1 1 d U . .
C12 C 0.8046(4) 0.28612(18) 0.2356(4) 0.0364(10) Uani 1 1 d U . .
C13 C 0.7448(4) 0.26425(18) 0.2371(4) 0.0363(10) Uani 1 1 d U . .
C14 C 0.7520(4) 0.22906(18) 0.2668(4) 0.0371(10) Uani 1 1 d U . .
C15 C 0.8275(4) 0.21763(17) 0.2977(4) 0.0366(10) Uani 1 1 d U . .
C16 C 0.8878(4) 0.23898(18) 0.2961(4) 0.0374(10) Uani 1 1 d U . .
C17 C 0.6893(5) 0.2046(2) 0.2687(4) 0.0473(12) Uani 1 1 d U . .
C18 C 0.6131(4) 0.2155(2) 0.2464(4) 0.0476(12) Uani 1 1 d U . .
H118 H 0.5929 0.2398 0.2281 0.057 Uiso 1 1 calc R . .
C19 C 0.6899(5) 0.1657(2) 0.2905(4) 0.0487(12) Uani 1 1 d U . .
H119 H 0.7334 0.1499 0.3090 0.058 Uiso 1 1 calc R . .
C20 C 0.6900(4) 0.8352(3) 0.4559(5) 0.0785(16) Uani 1 1 d U . .
H120 H 0.7315 0.8524 0.4735 0.094 Uiso 1 1 calc R . .
C21 C 0.6967(6) 0.7938(3) 0.4350(5) 0.0783(16) Uani 1 1 d U . .
C22 C 0.6181(6) 0.7846(3) 0.4134(5) 0.0786(16) Uani 1 1 d U . .
H122 H 0.5976 0.7602 0.3955 0.094 Uiso 1 1 calc R . .
C23 C 0.7564(3) 0.76987(16) 0.4329(3) 0.0739(15) Uani 1 1 d GU . .
C24 C 0.8296(4) 0.78358(14) 0.4638(3) 0.0744(15) Uani 1 1 d GU . .
C25 C 0.8895(2) 0.76204(18) 0.4620(3) 0.0747(15) Uani 1 1 d GU . .
C26 C 0.8762(3) 0.72678(17) 0.4293(3) 0.0747(15) Uani 1 1 d GU . .
C27 C 0.8030(4) 0.71306(14) 0.3984(3) 0.0742(15) Uani 1 1 d GU . .
C28 C 0.7431(2) 0.73461(18) 0.4002(3) 0.0738(15) Uani 1 1 d GU . .
C29 C 0.9441(3) 0.70496(17) 0.4244(3) 0.0811(16) Uani 1 1 d GDU . .
C30 C 1.0027(4) 0.72449(12) 0.4162(3) 0.0815(16) Uani 1 1 d GU . .
H30A H 1.0034 0.7519 0.4161 0.098 Uiso 1 1 calc R . .
C31 C 1.0603(3) 0.70390(17) 0.4082(3) 0.0815(16) Uani 1 1 d GDU . .
C32 C 1.0593(3) 0.66378(17) 0.4084(3) 0.0813(16) Uani 1 1 d GU . .
H32A H 1.0986 0.6497 0.4029 0.098 Uiso 1 1 calc R . .
C33 C 1.0007(4) 0.64424(12) 0.4166(3) 0.0813(16) Uani 1 1 d GDU . .
C34 C 0.9431(3) 0.66483(17) 0.4246(3) 0.0812(16) Uani 1 1 d GU . .
H34A H 0.9030 0.6515 0.4302 0.097 Uiso 1 1 calc R . .
C35 C 1.1277(4) 0.72656(19) 0.4040(3) 0.0792(16) Uani 1 1 d GDU . .
C36 C 1.2014(4) 0.71375(15) 0.4361(3) 0.0794(16) Uani 1 1 d GU . .
C37 C 1.2607(3) 0.7360(2) 0.4347(3) 0.0793(16) Uani 1 1 d GU . .
C38 C 1.2463(4) 0.77100(19) 0.4013(3) 0.0787(16) Uani 1 1 d GU . .
C39 C 1.1726(4) 0.78381(15) 0.3692(3) 0.0791(16) Uani 1 1 d GU . .

TABLE 2-continued

Compound [1] of Formula 1: Crystal Structure Unit Cell Data

```
C40 C 1.1133(3) 0.7616(2) 0.3705(3) 0.0793(16) Uani 1 1 d GU . .
C41 C 1.3120(6) 0.7945(3) 0.4018(5) 0.0810(16) Uani 1 1 d U . .
C42 C 1.3805(6) 0.7878(3) 0.4171(5) 0.0818(16) Uani 1 1 d U . .
H142 H 1.3999 0.7631 0.4344 0.098 Uiso 1 1 calc R . .
C43 C 1.3051(6) 0.8346(3) 0.3804(5) 0.0809(16) Uani 1 1 d U . .
H143 H 1.2614 0.8504 0.3663 0.097 Uiso 1 1 calc R . .
C44 C 1.0020(4) 0.59943(13) 0.4181(4) 0.0942(18) Uani 1 1 d GDU . .
C45 C 0.9374(3) 0.57974(19) 0.3781(4) 0.0943(18) Uani 1 1 d GU . .
C46 C 0.9365(3) 0.5396(2) 0.3778(3) 0.0943(18) Uani 1 1 d GU . .
C47 C 1.0002(4) 0.51918(13) 0.4175(4) 0.0940(18) Uani 1 1 d GU . .
C48 C 1.0647(3) 0.53887(19) 0.4575(3) 0.0945(18) Uani 1 1 d GU . .
C49 C 1.0656(3) 0.57899(19) 0.4578(3) 0.0945(18) Uani 1 1 d GU . .
C50 C 1.0020(7) 0.4748(3) 0.4179(6) 0.0879(17) Uani 1 1 d U . .
C51 C 0.9400(7) 0.4506(3) 0.3870(6) 0.0879(17) Uani 1 1 d U . .
H151 H 0.8899 0.4584 0.3609 0.105 Uiso 1 1 calc R . .
C52 C 1.0615(7) 0.4491(3) 0.4449(6) 0.0886(17) Uani 1 1 d U . .
H152 H 1.1123 0.4569 0.4680 0.106 Uiso 1 1 calc R . .
N1 N 0.9611(4) 0.58624(17) 0.2309(3) 0.0546(16) Uani 1 1 d U . .
H1A H 0.9334 0.6071 0.2166 0.066 Uiso 0.50 1 calc PR . .
N2 N 0.5748(4) 0.18635(16) 0.2552(3) 0.0477(11) Uani 1 1 d U . .
H2A H 0.5262 0.1863 0.2460 0.057 Uiso 0.50 1 calc PR . .
N3 N 0.6233(4) 0.15554(16) 0.2814(4) 0.0481(12) Uani 1 1 d U . .
H3A H 0.6101 0.1326 0.2903 0.058 Uiso 0.50 1 calc PR . .
N4 N 1.4260(5) 0.8133(2) 0.4103(4) 0.0820(16) Uani 1 1 d U . .
H4A H 1.4744 0.8113 0.4190 0.098 Uiso 1 1 calc R . .
N5 N 1.3776(5) 0.8448(2) 0.3852(4) 0.0808(16) Uani 1 1 d U . .
N6 N 0.6205(5) 0.8448(2) 0.4470(4) 0.0797(16) Uani 1 1 d U . .
H6A H 0.6054 0.8672 0.4562 0.096 Uiso 1 1 calc R . .
N7 N 0.5768(5) 0.8136(3) 0.4211(4) 0.0789(16) Uani 1 1 d U . .
N8 N 0.9654(5) 0.4138(5) 0.4017(5) 0.0881(17) Uani 1 1 d U . .
H8A H 0.9364 0.3932 0.3906 0.106 Uiso 1 1 calc R . .
N9 N 1.0399(5) 0.4130(2) 0.4352(5) 0.0883(17) Uani 1 1 d U . .
F1 F 0.8754(2) 0.47926(10) 0.1692(2) 0.0523(14) Uani 1 1 d U . .
F2 F 0.8740(2) 0.40322(10) 0.1712(2) 0.0518(14) Uani 1 1 d . . .
F3 F 0.7856(2) 0.31944(10) 0.2012(2) 0.0448(13) Uani 1 1 d . . .
F4 F 0.6739(2) 0.27940(10) 0.2050(2) 0.0500(14) Uani 1 1 d . . .
F5 F 0.8470(2) 0.18359(10) 0.3335(2) 0.0537(15) Uani 1 1 d . . .
F6 F 0.9587(2) 0.22493(10) 0.3313(2) 0.0495(14) Uani 1 1 d . . .
F7 F 0.8459(2) 0.81743(15) 0.4974(3) 0.091(2) Uani 1 1 d . . .
F8 F 0.9592(3) 0.77568(16) 0.4975(3) 0.0876(19) Uani 1 1 d . . .
F9 F 0.7866(3) 0.67996(16) 0.3667(3) 0.090(2) Uani 1 1 d . . .
F10 F 0.6748(3) 0.72175(16) 0.3718(3) 0.0851(19) Uani 1 1 d U . .
F11 F 1.2183(3) 0.68036(15) 0.4680(3) 0.0843(19) Uani 1 1 d . . .
F12 F 1.3274(4) 0.72139(17) 0.4614(3) 0.104(2) Uani 1 1 d . . .
F13 F 1.0450(4) 0.77574(15) 0.3364(3) 0.094(2) Uani 1 1 d . . .
F14 F 1.1570(3) 0.81620(14) 0.3365(3) 0.0865(19) Uani 1 1 d . . .
F15 F 0.8765(4) 0.52033(15) 0.3365(3) 0.101(2) Uani 1 1 d . . .
F16 F 0.8778(4) 0.59683(16) 0.3365(3) 0.098(2) Uani 1 1 d . . .
F17 F 1.1288(4) 0.59658(16) 0.4976(3) 0.097(2) Uani 1 1 d . . .
F18 F 1.1290(3) 0.52047(15) 0.4988(3) 0.091(2) Uani 1 1 d . . .
loop_
 _atom_site_aniso_label
 _atom_site_aniso_U_11
 _atom_site_aniso_U_22
 _atom_site_aniso_U_33
 _atom_site_aniso_U_23
 _atom_site_aniso_U_13
 _atom_site_aniso_U_12
C1 0.062(4) 0.031(2) 0.059(4) −0.0002(10) 0.012(3) 0.0006(9)
C2 0.061(4) 0.030(3) 0.058(4) 0.000 0.013(3) 0.000
C3 0.043(2) 0.030(2) 0.049(3) 0.000 0.029(2) 0.000
C4 0.042(3) 0.030(2) 0.049(3) −0.0001(8) 0.029(2) −0.0007(8)
C5 0.042(3) 0.030(2) 0.049(3) −0.0002(8) 0.029(2) −0.0006(8)
C6 0.042(3) 0.029(2) 0.049(3) 0.000 0.029(2) 0.000
C7 0.045(3) 0.024(2) 0.061(4) 0.000 0.032(3) 0.000
C8 0.045(3) 0.024(2) 0.060(4) −0.0002(8) 0.032(3) 0.0005(8)
C9 0.046(3) 0.024(2) 0.061(4) 0.0000(8) 0.031(3) 0.0002(8)
C10 0.046(3) 0.023(2) 0.061(4) 0.000 0.031(3) 0.000
C11 0.043(2) 0.0172(15) 0.056(3) −0.0040(16) 0.0258(18) −0.0014(14)
C12 0.042(2) 0.0169(15) 0.056(3) −0.0044(16) 0.0258(18) −0.0007(14)
C13 0.042(2) 0.0169(15) 0.056(3) −0.0048(16) 0.0258(18) 0.0000(14)
C14 0.043(2) 0.0177(15) 0.056(3) −0.0043(16) 0.0255(18) −0.0005(14)
C15 0.042(2) 0.0173(15) 0.056(3) −0.0035(16) 0.0260(18) −0.0019(14)
C16 0.043(2) 0.0180(15) 0.057(3) −0.0035(16) 0.0255(18) −0.0019(14)
C17 0.050(2) 0.0263(18) 0.073(3) −0.0042(19) 0.032(2) −0.0018(16)
C18 0.050(2) 0.0272(18) 0.073(3) −0.0041(19) 0.032(2) −0.0016(15)
C19 0.051(2) 0.0273(18) 0.074(3) −0.0044(19) 0.031(2) −0.0016(15)
C20 0.082(4) 0.088(3) 0.068(3) 0.009(3) 0.033(3) −0.037(3)
C21 0.083(4) 0.088(3) 0.068(3) 0.009(3) 0.033(3) −0.037(3)
C22 0.083(4) 0.088(3) 0.068(3) 0.009(3) 0.033(3) −0.037(3)
C23 0.063(3) 0.077(3) 0.078(4) 0.020(3) 0.023(3) −0.034(2)
C24 0.064(3) 0.077(3) 0.078(4) 0.019(3) 0.023(3) −0.034(2)
C25 0.064(3) 0.077(3) 0.078(4) 0.019(3) 0.022(3) −0.034(2)
C26 0.064(3) 0.078(3) 0.078(4) 0.019(3) 0.023(3) −0.033(2)
C27 0.063(3) 0.078(3) 0.078(4) 0.019(3) 0.023(3) −0.034(2)
C28 0.063(3) 0.077(3) 0.078(4) 0.019(3) 0.023(3) −0.034(2)
C29 0.090(4) 0.091(3) 0.065(3) −0.025(3) 0.034(3) −0.053(3)
C30 0.091(4) 0.091(3) 0.065(3) −0.025(3) 0.033(3) −0.053(3)
C31 0.091(4) 0.091(3) 0.065(3) −0.025(3) 0.033(3) −0.053(3)
C32 0.091(4) 0.091(3) 0.065(3) −0.025(3) 0.034(3) −0.053(3)
C33 0.091(4) 0.091(3) 0.065(3) −0.025(3) 0.034(3) −0.053(3)
C34 0.091(4) 0.091(3) 0.065(3) −0.025(3) 0.034(3) −0.053(3)
C35 0.114(4) 0.076(3) 0.058(4) −0.026(3) 0.044(3) −0.036(3)
C36 0.114(4) 0.076(3) 0.058(4) −0.026(3) 0.044(3) −0.036(3)
C37 0.114(4) 0.076(3) 0.058(4) −0.026(3) 0.044(3) −0.036(3)
C38 0.113(4) 0.075(3) 0.058(4) −0.027(3) 0.045(3) −0.037(3)
C39 0.114(4) 0.076(3) 0.058(4) −0.027(3) 0.044(3) −0.037(3)
C40 0.114(4) 0.076(3) 0.058(4) −0.026(3) 0.044(3) −0.037(3)
C41 0.082(4) 0.088(3) 0.090(4) −0.040(3) 0.053(3) −0.050(3)
C42 0.083(4) 0.088(3) 0.091(4) −0.040(3) 0.052(3) −0.050(3)
C43 0.082(4) 0.088(3) 0.091(4) −0.040(3) 0.053(3) −0.050(3)
C44 0.124(5) 0.095(4) 0.070(4) −0.026(3) 0.045(3) −0.075(3)
C45 0.124(5) 0.095(4) 0.071(4) −0.026(3) 0.045(3) −0.076(3)
C46 0.124(5) 0.095(4) 0.071(4) −0.026(3) 0.045(3) −0.076(3)
C47 0.124(5) 0.095(4) 0.071(4) −0.026(3) 0.046(3) −0.076(3)
C48 0.124(5) 0.095(4) 0.071(4) −0.026(3) 0.045(3) −0.075(3)
C49 0.124(5) 0.095(4) 0.071(4) −0.027(3) 0.045(3) −0.075(3)
C50 0.118(4) 0.062(3) 0.110(4) −0.025(3) 0.072(4) −0.051(3)
C51 0.118(4) 0.062(3) 0.110(4) −0.025(3) 0.072(4) −0.051(3)
C52 0.118(4) 0.062(3) 0.110(4) −0.025(3) 0.072(4) −0.051(3)
N1 0.062(4) 0.031(2) 0.059(4) −0.0005(13) 0.011(3) 0.0016(13)
N2 0.050(2) 0.0270(17) 0.073(3) −0.0040(19) 0.032(2) −0.0017(15)
N3 0.050(2) 0.0270(17) 0.074(3) −0.0039(19) 0.032(2) −0.0023(15)
N4 0.083(4) 0.089(3) 0.091(4) −0.040(3) 0.052(3) −0.049(3)
N5 0.082(4) 0.088(3) 0.091(4) −0.040(3) 0.053(3) −0.049(3)
N6 0.083(4) 0.088(3) 0.069(3) 0.008(3) 0.032(3) −0.036(3)
N7 0.083(4) 0.088(3) 0.069(3) 0.008(3) 0.032(3) −0.036(3)
N8 0.117(4) 0.062(3) 0.110(4) −0.025(3) 0.072(4) −0.051(3)
N9 0.118(4) 0.062(3) 0.111(4) −0.025(3) 0.072(4) −0.051(3)
F1 0.052(3) 0.022(2) 0.080(4) 0.004(2) 0.023(2) 0.0020(17)
F2 0.042(3) 0.027(2) 0.077(4) −0.009(2) 0.012(3) −0.0023(19)
F3 0.055(3) 0.023(2) 0.069(4) 0.007(2) 0.038(3) 0.0068(19)
F4 0.047(3) 0.025(2) 0.084(4) 0.006(3) 0.033(3) −0.0053(19)
F5 0.048(3) 0.018(2) 0.088(4) 0.017(3) 0.019(3) 0.0036(18)
F6 0.041(3) 0.026(2) 0.081(4) 0.011(3) 0.024(2) 0.0040(19)
F7 0.114(5) 0.074(4) 0.120(6) −0.018(4) 0.083(4) −0.048(3)
F8 0.063(4) 0.104(4) 0.109(5) −0.021(4) 0.048(3) −0.041(3)
F9 0.106(5) 0.084(4) 0.085(5) −0.027(3) 0.044(3) −0.061(3)
F10 0.084(3) 0.103(4) 0.067(4) −0.002(3) 0.028(3) −0.068(3)
F11 0.092(4) 0.077(4) 0.076(5) −0.011(3) 0.024(3) −0.039(3)
F12 0.124(6) 0.089(4) 0.111(6) −0.047(4) 0.061(4) −0.062(4)
F13 0.116(5) 0.080(4) 0.094(5) −0.004(3) 0.051(3) −0.046(4)
F14 0.097(5) 0.062(3) 0.093(5) −0.015(3) 0.029(3) −0.048(3)
F15 0.113(5) 0.068(4) 0.102(6) −0.015(3) 0.021(4) −0.053(3)
F16 0.105(5) 0.082(4) 0.120(6) −0.015(4) 0.061(4) −0.041(4)
F17 0.141(6) 0.075(4) 0.069(5) −0.014(3) 0.036(4) −0.048(4)
F18 0.113(5) 0.073(4) 0.092(5) −0.027(3) 0.044(4) −0.043(3)
_geom_special_details
;
 All esds (except the esd in the dihedral angle between two l.s.
planes)
 are estimated using the full covariance matrix. The cell esds are
taken
 into account individually in the estimation of esds in distances,
angles
 and torsion angles; correlations between esds in cell parameters
are only
 used when they are defined by crystal symmetry. An approximate
(isotropic)
 treatment of cell esds is used for estimating esds involving l.s.
planes.
;
loop_
 _geom_bond_atom_site_label_1
 _geom_bond_atom_site_label_2
 _geom_bond_distance
```

TABLE 2-continued

Compound [1] of Formula 1: Crystal Structure Unit Cell Data

_geom_bond_site_symmetry_2
_geom_bond_publ_flag
C1 N1 1.345(9) . ?
C1 C2 1.428(9) . ?
C1 H101 0.9500 . ?
C2 C1 1.428(9) 2_755 ?
C2 C3 1.508(13) . ?
C3 C4 1.401(9) 2_755 ?
C3 C4 1.401(9) . ?
C4 F1 1.341(8) . ?
C4 C5 1.368(9) . ?
C5 F2 1.348(8) . ?
C5 C6 1.408(9) . ?
C6 C5 1.408(9) 2_755 ?
C6 C7 1.491(13) . ?
C7 C8 1.398(8) . ?
C7 C8 1.398(8) 2_755 ?
C8 C9 1.391(9) . ?
C8 H108 0.9500 . ?
C9 C10 1.423(8) . ?
C9 C11 1.446(9) . ?
C10 C9 1.423(8) 2_755 ?
C10 H110 0.9500 . ?
C11 C12 1.368(10) . ?
C11 C16 1.395(9) . ?
C12 F3 1.350(8) . ?
C12 C13 1.391(9) . ?
C13 C14 1.365(9) . ?
C13 F4 1.376(8) . ?
C14 C15 1.402(10) . ?
C14 C17 1.492(10) . ?
C15 F5 1.386(8) . ?
C15 C16 1.392(9) . ?
C16 F6 1.371(8) . ?
C17 C18 1.408(10) . ?
C17 C19 1.428(10) . ?
C18 N2 1.309(9) . ?
C18 H118 0.9500 . ?
C19 N3 1.270(9) . ?
C19 H119 0.9500 . ?
C20 N6 1.320(12) . ?
C20 C21 1.528(14) . ?
C20 H120 0.9500 . ?
C21 C23 1.436(12) . ?
C21 C22 1.437(13) . ?
C22 N7 1.335(13) . ?
C22 H122 0.9500 . ?
C23 C24 1.3900 . ?
C23 C28 1.3900 . ?
C24 F7 1.356(6) . ?
C24 C25 1.3900 . ?
C25 F8 1.349(6) . ?
C25 C26 1.3900 . ?
C26 C27 1.3900 . ?
C26 C29 1.554(5) . ?
C27 F9 1.315(6) . ?
C27 C28 1.3900 . ?
C28 F10 1.296(6) . ?
C29 C30 1.3900 . ?
C29 C34 1.3900 . ?
C30 C31 1.3900 . ?
C30 H30A 0.9500 . ?
C31 C32 1.3900 . ?
C31 C35 1.554(5) . ?
C32 C33 1.3900 . ?
C32 H32A 0.9500 . ?
C33 C34 1.3900 . ?
C33 C44 1.553(6) . ?
C34 H34A 0.9500 . ?
C35 C36 1.3900 . ?
C35 C40 1.3900 . ?
C36 F11 1.327(7) . ?
C36 C37 1.3900 . ?
C37 F12 1.290(8) . ?
C37 C38 1.3900 . ?
C38 C39 1.3900 . ?
C38 C41 1.503(10) . ?
C39 F14 1.303(7) . ?
C39 C40 1.3900 . ?
C40 F13 1.329(8) . ?
C41 C42 1.253(14) . ?
C41 C43 1.456(14) . ?
C42 N4 1.295(11) . ?
C42 H142 0.9500 . ?
C43 N5 1.406(11) . ?
C43 H143 0.9500 . ?
C44 C45 1.3900 . ?
C44 C49 1.3900 . ?
C45 F16 1.298(8) . ?
C45 C46 1.3900 . ?
C46 F15 1.337(7) . ?
C46 C47 1.3900 . ?
C47 C48 1.3900 . ?
C47 C50 1.538(11) . ?
C48 F18 1.373(8) . ?
C48 C49 1.3900 . ?
C49 F17 1.337(7) . ?
C50 C52 1.387(15) . ?
C50 C51 1.401(13) . ?
C51 N8 1.356(13) . ?
C51 H151 0.9500 . ?
C52 N9 1.311(11) . ?
C52 H152 0.9500 . ?
N1 N1 1.405(13) 2_755 ?
N1 H1A 0.8800 . ?
N2 N3 1.387(8) . ?
N2 H2A 0.8800 . ?
N3 H3A 0.8800 . ?
N4 N5 1.402(11) . ?
N4 H4A 0.8800 . ?
N6 N7 1.350(10) . ?
N6 H6A 0.8800 . ?
N8 N9 1.335(12) . ?
N8 H8A 0.8800 . ?
loop_
_geom_angle_atom_site_label_1
_geom_angle_atom_site_label_2
_geom_angle_atom_site_label_3
_geom_angle
_geom_angle_site_symmetry_1
_geom_angle_site_symmetry_3
_geom_angle_publ_flag
N1 C1 C2 104.4(8) . . ?
N1 C1 H101 127.8 . . ?
C2 C1 H101 127.8 . . ?
C1 C2 C1 110.3(10) 2_755 . ?
C1 C2 C3 124.9(5) 2_755 . ?
C1 C2 C3 124.9(5) . . ?
C4 C3 C4 115.0(9) 2_755 . ?
C4 C3 C2 122.5(5) 2_755 . ?
C4 C3 C2 122.5(5) . . ?
F1 C4 C5 118.1(7) . . ?
F1 C4 C3 119.3(6) . . ?
C5 C4 C3 122.5(8) . . ?
F2 C5 C4 118.0(7) . . ?
F2 C5 C6 118.9(7) . . ?
C4 C5 C6 123.0(8) . . ?
C5 C6 C5 114.0(9) . 2_755 ?
C5 C6 C7 123.0(5) . . ?
C5 C6 C7 123.0(5) 2_755 . ?
C8 C7 C8 119.3(9) . 2_755 ?
C8 C7 C6 120.3(4) . . ?
C8 C7 C6 120.3(4) 2_755 . ?
C9 C8 C7 122.0(7) . . ?
C9 C8 H108 119.0 . . ?
C7 C8 H108 119.0 . . ?
C8 C9 C10 117.0(7) . . ?
C8 C9 C11 123.6(6) . . ?
C10 C9 C11 119.2(6) . . ?
C9 C10 C9 122.5(9) . 2_755 ?
C9 C10 H110 118.7 2_755 . ?
C9 C10 H110 118.7 . . ?
C12 C11 C16 113.5(7) . . ?
C12 C11 C9 123.2(7) . . ?
C16 C11 C9 123.1(7) . . ?
F3 C12 C11 120.7(6) . . ?

TABLE 2-continued

Compound [1] of Formula 1: Crystal Structure Unit Cell Data

F3 C12 C13 115.8(6) . . ?
C11 C12 C13 123.2(7) . . ?
C14 C13 F4 118.7(6) . . ?
C14 C13 C12 124.7(7) . . ?
F4 C13 C12 116.6(6) . . ?
C13 C14 C15 112.0(6) . . ?
C13 C14 C17 126.2(7) . . ?
C15 C14 C17 121.7(6) . . ?
F5 C15 C16 115.1(6) . . ?
F5 C15 C14 121.0(6) . . ?
C16 C15 C14 123.9(7) . . ?
F6 C16 C11 120.6(6) . . ?
F6 C16 C15 117.2(6) . . ?
C11 C16 C15 122.2(7) . . ?
C18 C17 C19 103.8(7) . . ?
C18 C17 C14 125.9(7) . . ?
C19 C17 C14 130.3(7) . . ?
N2 C18 C17 108.4(7) . . ?
N2 C18 H118 125.8 . . ?
C17 C18 H118 125.8 . . ?
N3 C19 C17 109.6(7) . . ?
N3 C19 H119 125.2 . . ?
C17 C19 H119 125.2 . . ?
N6 C20 C21 113.1(9) . . ?
N6 C20 H120 123.4 . . ?
C21 C20 H120 123.5 . . ?
C23 C21 C22 128.1(9) . . ?
C23 C21 C20 135.8(8) . . ?
C22 C21 C20 96.0(9) . . ?
N7 C22 C21 113.3(10) . . ?
N7 C22 H122 123.3 . . ?
C21 C22 H122 123.4 . . ?
C24 C23 C28 120.0 . . ?
C24 C23 C21 117.5(6) . . ?
C28 C23 C21 122.5(6) . . ?
F7 C24 C23 122.4(5) . . ?
F7 C24 C25 117.6(5) . . ?
C23 C24 C25 120.0 . . ?
F8 C25 C24 116.6(5) . . ?
F8 C25 C26 123.2(5) . . ?
C24 C25 C26 120.0 . . ?
C25 C26 C27 120.0 . . ?
C25 C26 C29 118.3(5) . . ?
C27 C26 C29 121.6(5) . . ?
F9 C27 C26 122.9(6) . . ?
F9 C27 C28 117.1(6) . . ?
C26 C27 C28 120.0 . . ?
F10 C28 C27 120.1(6) . . ?
F10 C28 C23 119.9(6) . . ?
C27 C28 C23 120.0 . . ?
C30 C29 C34 120.0 . . ?
C30 C29 C26 121.7(5) . . ?
C34 C29 C26 118.2(5) . . ?
C29 C30 C31 120.0 . . ?
C29 C30 H30A 120.0 . . ?
C31 C30 H30A 120.0 . . ?
C30 C31 C32 120.0 . . ?
C30 C31 C35 118.7(5) . . ?
C32 C31 C35 121.2(5) . . ?
C33 C32 C31 120.0 . . ?
C33 C32 H32A 120.0 . . ?
C31 C32 H32A 120.0 . . ?
C32 C33 C34 120.0 . . ?
C32 C33 C44 118.8(5) . . ?
C34 C33 C44 121.2(5) . . ?
C33 C34 C29 120.0 . . ?
C33 C34 H34A 120.0 . . ?
C29 C34 H34A 120.0 . . ?
C36 C35 C40 120.0 . . ?
C36 C35 C31 121.6(6) . . ?
C40 C35 C31 118.3(6) . . ?
F11 C36 C37 117.5(6) . . ?
F11 C36 C35 122.5(6) . . ?
C37 C36 C35 120.0 . . ?
F12 C37 C38 122.7(6) . . ?
F12 C37 C36 117.2(6) . . ?
C38 C37 C36 120.0 . . ?
C37 C38 C39 120.0 . . ?

TABLE 2-continued

Compound [1] of Formula 1: Crystal Structure Unit Cell Data

C37 C38 C41 118.4(7) . . ?
C39 C38 C41 121.6(7) . . ?
F14 C39 C38 121.6(6) . . ?
F14 C39 C40 118.4(6) . . ?
C38 C39 C40 120.0 . . ?
F13 C40 C39 115.2(6) . . ?
F13 C40 C35 124.7(6) . . ?
C39 C40 C35 120.0 . . ?
C42 C41 C43 102.5(9) . . ?
C42 C41 C38 134.5(11) . . ?
C43 C41 C38 123.0(10) . . ?
C41 C42 N4 122.3(12) . . ?
C41 C42 H142 118.8 . . ?
N4 C42 H142 118.8 . . ?
N5 C43 C41 104.8(10) . . ?
N5 C43 H143 127.6 . . ?
C41 C43 H143 127.6 . . ?
C45 C44 C49 120.0 . . ?
C45 C44 C33 118.3(6) . . ?
C49 C44 C33 121.7(6) . . ?
F16 C45 C46 116.5(6) . . ?
F16 C45 C44 123.3(6) . . ?
C46 C45 C44 120.0 . . ?
F15 C46 C45 120.6(6) . . ?
F15 C46 C47 119.3(6) . . ?
C45 C46 C47 120.0 . . ?
C46 C47 C48 120.0 . . ?
C46 C47 C50 121.7(7) . . ?
C48 C47 C50 118.3(7) . . ?
F18 C48 C49 117.0(6) . . ?
F18 C48 C47 123.0(6) . . ?
C49 C48 C47 120.0 . . ?
F17 C49 C48 117.7(6) . . ?
F17 C49 C44 122.3(6) . . ?
C48 C49 C44 120.0 . . ?
C52 C50 C51 103.3(10) . . ?
C52 C50 C47 131.0(9) . . ?
C51 C50 C47 125.6(11) . . ?
N8 C51 C50 106.6(11) . . ?
N8 C51 H151 126.7 . . ?
C50 C51 H151 126.7 . . ?
N9 C52 C50 112.7(11) . . ?
N9 C52 H152 123.7 . . ?
C50 C52 H152 123.7 . . ?
C1 N1 N1 110.4(5) . 2_755 ?
C1 N1 H1A 124.8 . . ?
N1 N1 H1A 124.8 2_755 . ?
C18 N2 N3 109.0(7) . . ?
C18 N2 H2A 125.5 . . ?
N3 N2 H2A 125.5 . . ?
C19 N3 N2 109.1(6) . . ?
C19 N3 H3A 125.4 . . ?
N2 N3 H3A 125.4 . . ?
C42 N4 N5 101.5(9) . . ?
C42 N4 H4A 129.2 . . ?
N5 N4 H4A 129.3 . . ?
C43 N5 N4 108.9(8) . . ?
C20 N6 N7 107.0(9) . . ?
C20 N6 H6A 126.5 . . ?
N7 N6 H6A 126.5 . . ?
C22 N7 N6 110.6(9) . . ?
N9 N8 C51 111.3(8) . . ?
N9 N8 H8A 124.4 . . ?
C51 N8 H8A 124.4 . . ?
C52 N9 N8 105.9(10) . . ?

| | |
|---|---|
| _diffrn_measured_fraction_theta_max | 0.892 |
| _diffrn_reflns_theta_full | 13.96 |
| _diffrn_measured_fraction_theta_full | 0.892 |
| _refine_diff_density_max | 0.849 |
| _refine_diff_density_min | −0.501 |
| _refine_diff_density_rms | 0.167 |

Figure 2:
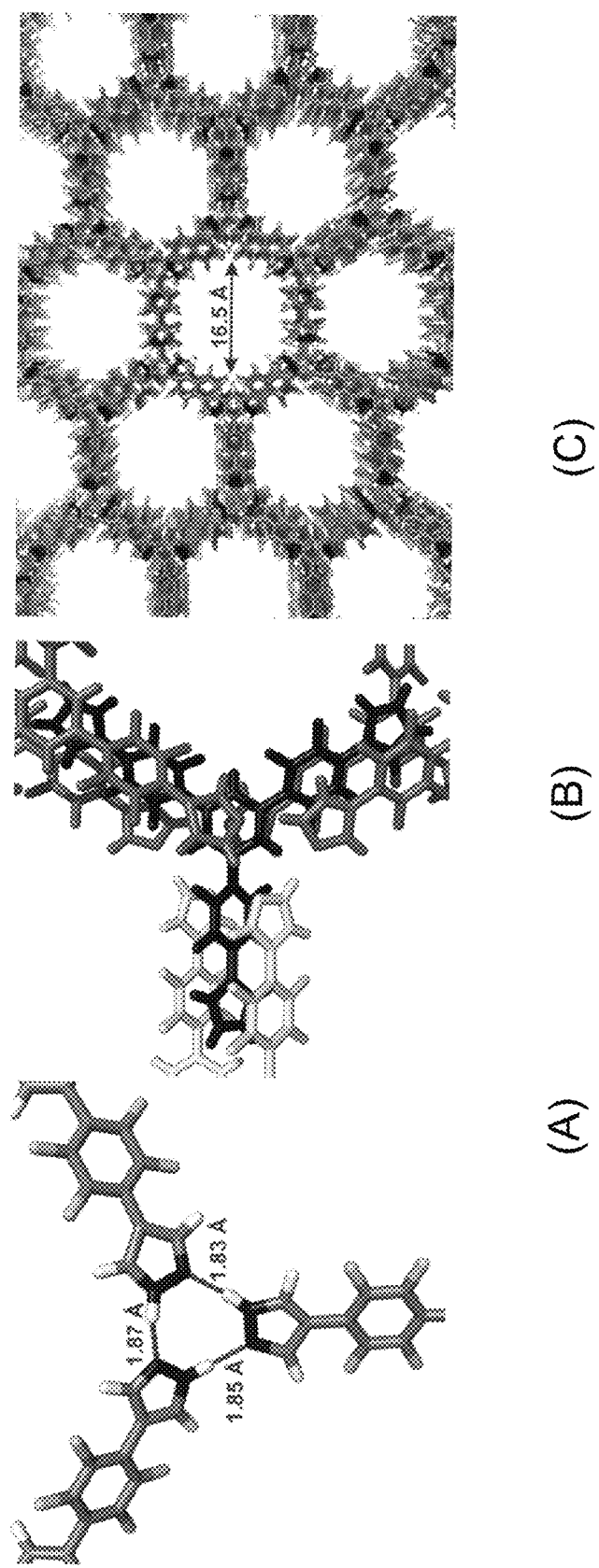
FIG. 2: depicts the crystal structure of compound 1 (unit cell data is listed in Table 2) in accordance with an embodiment of this invention. Three pyrazoles come together in each of the layers (left (A)) forming a triplet of hydrogen bonds. Each pyrazole engages in [π . . . π] stacking interactions with six of its neighbors, shown in different colors/greyscale (center (B)). Overall, a hexagonal network results, with infinite fluorine-lined channels (about 16.5 Å in diameter protruding throughout the structure (right (C))

Structural aspects of the crystal structure of compound 1 are shown in FIG. 2. The three arms of 1 twist in a propeller-like fashion out of the plane of the central ring, forming angles of 33.7, 33.8 and 46.3°. Each molecule of 1 establishes short contacts with twelve of its neighbors: six

[N—H . . . N] hydrogen bonds, which create a hexagonal two-dimensional lattice and six [π . . . π] stacking arrangements which propagate these layers into the third dimension.

Pyrazoles at the end of each arm of 1 establish hydrogen bonds with two adjacent molecules (FIG. 2, left (A)). These three bonds are close to each other in length (N . . . H distances: 1.83, 1.85 and 1.87 Å; N . . . N distances: 2.78, 2.83 and 2.87 Å). Control of inter-layer relationships is achieved through [π . . . π] stacking of the electron-poor tetrafluorinated aromatic rings with the electron-rich pyrazoles (FIG. 2(B)), but this relationship is highly unsymmetric. In each molecule of 1, the most deplanarized of the three arms engages in the predicted [π . . . π] stacking with its "top" and "bottom" neighbors (shown in yellow (or left arm) in FIG. 2(B)). These stacks are symmetric, with centroid-centroid distances between the pyrazole and tetrafluorobenzene rings being 3.68 Å (for the pair closer to the center of the black molecule in FIG. 2(B) (central compound in the overlay)) and 3.69 Å (for the pair further away from the center). The angle between the adjacent planes of pyrazole and tetrafluorobenzene rings is 11.2° (for the inner pair) and 9.7° (for the outer pair). In the other two "arms" of compound 1 the top and the bottom neighbors are no longer equivalent. One (shown in red in FIG. 2(B)) establishes a pair of [π . . . π] stacking interactions characterized by centroid-centroid distances of 3.42 and 3.50 Å and interplanar angles of 10.3 and 11.4° respectively for the inner and outer pairs. The other neighbor (shown in blue (right arm) in FIG. 2(B)) establishes a slipped [π . . . π] stacking, in which centroids of tetrafluorobenzene and pyrazole rings reside quite far from each other at 5.28 Å. In fact, the closest two rings are two tetrafluorobenzenes, with centroid-centroid distance of 4.08 Å, and essentially parallel arrangement of the planes (interplanar angle of 0.49°). This arrangement which is repeated in the third arm of 1, is caused by the steric mismatch of the central benzene ring with the "pyrazole triad" that resides above it in the next layer, and so one arm of the molecule must sacrifice favorable [π . . . π] stacking interactions to accommodate this dimensional difference.

In some embodiments, a three-dimensional network is formed, with infinite one-dimensional channels protruding throughout the crystal; these channels are lined with fluorines and have a diameter of about 16.5 Å. The disclosed structural elements of 1 produce the infinite porous structure: in some embodiments a pyrazole is needed to lower the solubility (e.g. its tetrazole analog is much too soluble to crystallize under similar conditions) and to establish the hydrogen bonding pattern within the two-dimensional layers. In some embodiments, a perfluorinated ring is also needed, to generate favorable electronic complementarity between the two motifs. In some embodiments the trigonal structure of 1 ensures that the pores will be hexagonal in nature.

In some embodiments, compound 1 is white in color and stable to solvents, acids and bases, and in another embodiment displays no crystal decomposition or dissolution in dichloromethane, hexanes, toluene or acetone after 30 days. In another embodiment compound 1 is stable to deionized water at 25° C. for at least 30 days, and stable at 100° C. for at least 7 days. In further embodiments compound 1 also was stable in acids (1M HCl) and bases (2M NaOH) at 25° C. for at least 30 days, in other embodiments is sparingly soluble in DMSO at 25° C., and in a further still embodiment its solubility in DMSO improves with increased temperature.

Prior art organic molecules form crystal structures which have large empty spaces occupied by solvent molecules, however they collapse upon solvent removal. Compounds of the current disclosure (such as in one embodiment, compound 1) is different in that respect, and remains stable. Its single-crystal X-ray structure (of compound 1) was refined from data collected at low temperature revealing significant electron density within the pores attributed to disordered solvent. In some embodiments, all solvent leaves the pores within minutes at 25° C. without loss of crystallinity, and no collapse of structure occurs in contrast to the molecules of the prior art. Thermogravimetric analysis (TGA, FIG. 3A) of 1 confirmed the absence of solvent in the crystal: after air-drying, heating of this material does not result in any weight loss up until 360° C., which is significantly above the boiling points of all the solvents used in the synthesis.

In some embodiments of the synthesis described herein, perfluorinated material associates very weakly with the hydrophilic solvents DMF, MeOH and residual $H_2O$—used in its synthesis. At 360° C., compound 1 looses about 11% of its weight, which in some embodiments is attributed to the removal of an HCN molecule (−11.25%) from each of the three arms of 1; such behavior has precedent in mass spectrometry of pyrazoles.[12] Slightly above 400° C., the second stage of weight-loss begins; this step continues until 900° C., where measurement was stopped. At 900° C., 50% of the original weight of 1 is still present in the sample; 30 carbon atoms of compound 1 (left over after the loss of three HCN molecules) carry exactly half of the compound's weight, so in one embodiment compound 1 may eventually thermolyse into graphite.

Figure 3:
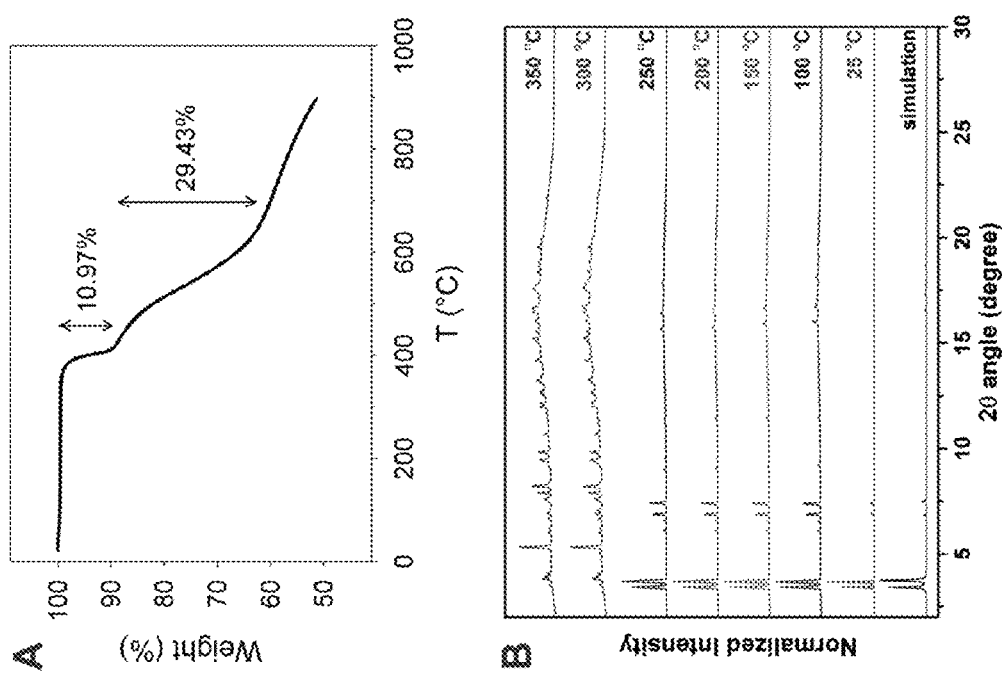
FIG. 3: depicts plots illustrating the thermal stability of compound 1 in accordance with an embodiment of this invention. (A) depicts the Thermo-Gravimetric Analysis (TGA) and shows no weight loss until 360° C., indicating that no solvent was included in the crystal structure of compound 1 (Table 2). Between 360° C. and 400° C., compound 1 loses about 11% of its weight, due to the loss of three molecules of HCN. Beyond 400° C., slow decomposition of the material ensues. (B) shows a variable temperature Powder X-ray Diffraction (PXRD) which revealed no change in structure until at least 250° C. Beyond that temperature, in some embodiments an irreversible phase change occurs, transforming compound 1 into a new crystalline phase.

In a further embodiment described herein, the structural changes that occur with heating were elucidated, and a variable-temperature powder X-ray diffraction (PXRD) study of compound 1 was also performed herein; results shown in FIG. 3B indicate that the crystal phase does not change until at least 250° C. At higher temperatures, the PXRD pattern changes irreversibly, but the material in some embodiments is largely crystalline, although in some other embodiments the uneven PXRD pattern baseline may suggest an amorphous contribution. Differential scanning calorimetry (DSC) measurements show a sharp peak at 285° C., consistent with a phase change. In some embodiments, the difference between the apparent decomposition temperatures obtained from TGA and PXRD measurements may be rationalized by the fact that TGA is a dynamic measurement, as well as the fact that the phase change observed by PXRD is not associated with weight loss.

Further, in some embodiments, compound 1 can be sublimed in high vacuum (0.03 mmHg) at 250° C. during the course of 48 hours. The obtained material is crystalline, but its PXRD pattern matches neither the one of the as-synthesized sample of 1, nor the one observed after 1 was heated to >300° C.; this new phase is also non-porous. In one embodiment, this finding, along with the above-mentioned irreversible thermal phase change indicate that the porous structure of 1 is a kinetic rather than a thermodynamic product.

Figure 4:
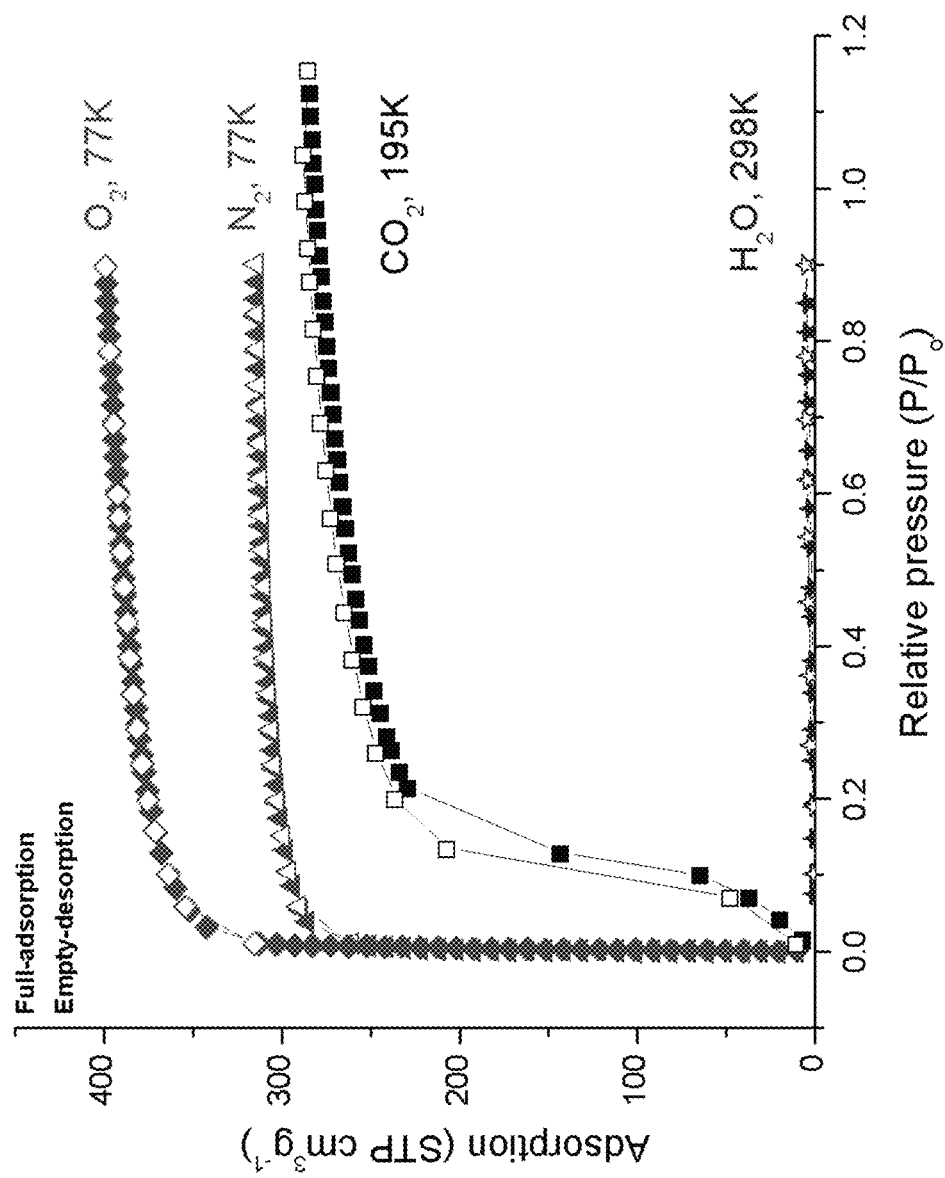
FIG. 4: is a plot depicting gas sorption in crystals of compound 1 in accordance with an embodiment of this invention. Crystals of compound 1 take up $N_2$, $O_2$ and $CO_2$, but not $H_2O$ vapor (flat-line) even at 90% relative humidity.

In some embodiments, the gas sorption within the pores of compound 1 was probed using nitrogen, oxygen, and carbon dioxide as guest molecules. Based on nitrogen adsorption isotherm (FIG. 4), in some embodiments, the Brunauer-Emmett-Teller (BET) surface area of 1 is 1,159 $m^2$ $g^{-1}$. In another embodiment, the uptake of $CO_2$ at 195 K by compound 1 is approx. 270 $cm^3$ $g^{-1}$; and in a further embodiment at 80% relative humidity, crystals of 1 take up a negligible amount of $H_2O$ vapor, consistent with their highly hydrophobic character. Hydrophobic behavior[13] was also confirmed by contact angle measurements with $H_2O$, which revealed a contact angle of 132±1°. Similar hydrophobicity in MOFs constructed from fluorinated ligands has been observed[14-16].

Figure 5:
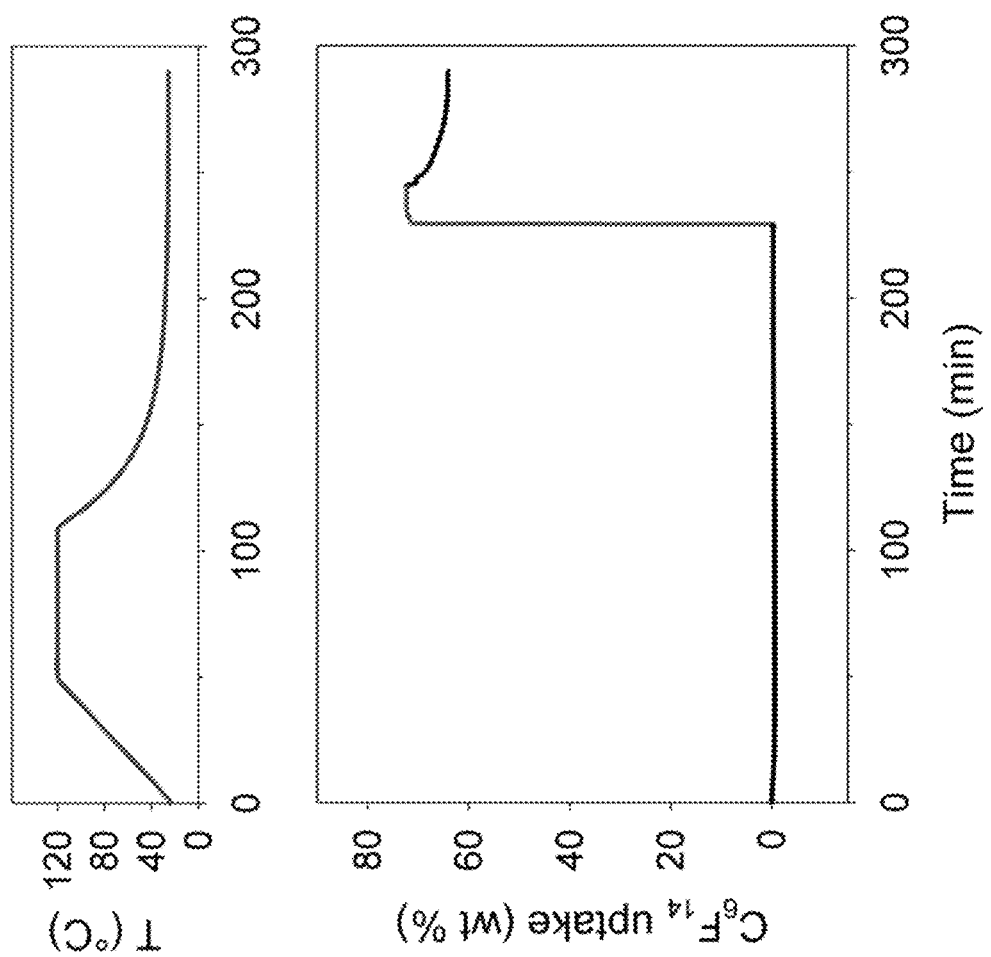
FIG. 5: is a plot depicting sorption of perfluorohexane ($C_6F_{14}$) in crystals of compound 1 in accordance with an embodiment of this invention. Crystals of compound 1 take up close to 75% of their own weight (weight capacity) in perfluorohexane. The top chart shows the temperature program used, while the bottom chart illustrates the uptake of the guest as the function of time. In the bottom chart, the black lines indicate the parts of the program when 1 was exposed only to nitrogen stream, while the green (vertical component of the line) describes the section of the program when nitrogen carrying $C_6F_{14}$ vapors was passed over compound 1.

In some embodiments, adsorption of liquid guests within the pores of 1 was followed by TGA, and in some embodiments fluorocarbons, hydrocarbons, and Freons[14] are defined as guests. The experimental design is illustrated in FIG. 5, utilizing perfluorohexane ($C_6F_{14}$). Crystals of 1 were placed into the thermogravimetric balance and then heated to 120° C., at which temperature they were kept for 1 h. The objective of this step was to remove any residual solvent and/or volatile guests from the pores of 1. The heating was then discontinued and the material was allowed to cool down to room temperature. At that point, the flow of carrier gas was switched from pure nitrogen to nitrogen that was allowed to pass over a reservoir containing the liquid guest of interest. Using this methodology, uptake capacities for several hydrocarbon and halogenated hydrocarbon guests were measured as shown in Table 1. Reversibility of this process was confirmed by performing over 20 adsorption/desorption cycles with perfluorohexane as the guest; no loss of capacity was observed. In the case of fluorinated guests, the uptake in some embodiments are very fast: compound 1 becomes saturated with perfluorohexane in less than 20 seconds. The last three guests are of interest because of their high greenhouse gas potential, which is hundreds to thousands of times more severe than that of $CO_2$.[15] The high weight sorption percentages profit from the absence of metals in the lightweight structure of 1.

In a further embodiment, a synthetic method for compound 5 is provided: wherein: A 100 mL screw cap pressure vessel was equipped with magnetic stir bar and charged with CuCl (3.35 g, 33.5 mmol) and t-BuOLi (2.68 g, 33.5 mmol). Dry DMF (40 mL) was added, and the vessel was sealed, taken out of the glovebox, sonicated for 5 min and vigorously stirred at 25° C. for 1 h. Pressure vessel was then placed back inside the glovebox, and compound 4 (15.6 g, 34.0 mmol) was added in one portion. After that, the reaction vessel was sealed again, taken out of the glovebox, sonicated for 5 min and vigorously stirred at 25° C. for 1 h. Pressure vessel was placed back inside glovebox. Catalyst $Pd(PPh_3)_4$ (347 mg, 0.30 mmol) was added, followed by 1,3,5-triiodobenzene (4.56 g, 10 mmol). Reaction vessel was sealed, taken out of the glovebox and placed inside an oil bath preheated to 100° C., where it was stirred vigorously for 12 h. Reaction mixture was cooled to 25° C., diluted with $CH_2Cl_2$ (150 mL) and 3% aqueous citric acid (100 mL) was added. After filtration through a plug of Celite, filter cake was washed with additional $CH_2Cl_2$ (3×25 mL). Combined organic layers were separated and washed with deionized water (5×100 mL), followed by brine (100 mL). Organic layer was dried over anhydrous $MgSO_4$, filtered and dry-absorbed on silica gel. After purification by column chromatography on silica gel using $CH_2Cl_2$/hexanes as eluent and evaporation of the fractions containing the product, compound 5 was obtained as a tan oil (13.5 g, 93%). $^1$H NMR (400 MHz, $CDCl_3$) δ8.20 (s, 1H), 7.96 (s, 1H), 7.67 (s, 1H) 7.40-7.30 (m, 27H), 7.22-7.15 (m, 18H) ppm. $^{19}$F NMR (376 MHz, $CDCl_3$) δ−140.6 to −140.8 (m, 6F), −144.6 to −144.9 (m, 6F) ppm. This compound was used crude in the next step.

In another embodiment, a method of synthesis is provided for compound 6, wherein: a 250 mL flask equipped with magnetic stir bar was charged with compound 5 (13.3 g, 9.20 mmol) and $CHCl_3$ (140 mL). The resulting clear solution was stirred vigorously and then trifluoroacetic acid (12 mL) was added, resulting in a color change from colorless to yellow. Stirring was continued at 25° C. for 20 h. Resulting salt that was formed during the reaction was filtered off and washed with fresh $CHCl_3$ (3×50 mL). Obtained light tan solid was dried in vacuum for 2 h. A 250 mL flask equipped with magnetic stir bar was charged with this isolated salt and $CH_2Cl_2$ (100 mL) was added. Resulting suspension was treated with $Et_3N$ (9 mL), followed by the addition of DMAP (1.22 g, 10.0 mmol). To the open flask, $Boc_2O$ (12.0 g, 55 mmol) was added via syringe over 5 min. Rapid evolution of $CO_2$ is observed during the addition. After addition of $Boc_2O$ was complete, reaction flask was capped with a septum connected to a bubbler. Reaction mixture was stirred vigorously at 25° C. until the evolution of $CO_2$ ceased (typically 12-36 h). Upon completion, reaction mixture was dry-absorbed on silica gel. After purification by column chromatography on silica gel (using $EtOAc/CH_2Cl_2$ as eluent) and evaporation of the fractions containing the product, compound 6 was obtained as a white solid (5.3 g, 56% over two steps), mp 350° C. (decomposition). $^1$H NMR (500 MHz, $CDCl_3$) δ8.65 (s, 3H), 8.25 (s, 3H), 7.78 (s, 3H), 1.71 (s, 27H) ppm. $^{19}$F NMR (470 MHz, $CDCl_3$) δ−139.8 to −140.0 (m, 6F), −143.7 to −143.9 (m, 6F) ppm. FT-IR: 3213 (s, $v_{N=C-H}$), 3140 (s, $v_{N-C-H}$), 2985 (m, $v_{C=C-H}$), 1794 (m, $v_{C=O}$), 1759 (m, $v_{C=N}$), 1581 (s, $v_{C=C}$), 1498 (s), 1481 (s), 1400 (s), 1375 (s), 1348 (s), 1296 (s), 1246 (s), 1153 (s), 1033 (m), 972 (s), 845 (s) cm$^{-1}$. HRMS (ESI$^+$ mode): Calculated for $C_{48}H_{36}F_{12}N_6O_6Na$: 1043.23970. Found: 1043.23810.

In further embodiment, a method of synthesis is provided for compound 1, wherein compound 6 (200 mg, 0.20 mmol) was added to a 100 mL glass bottle. Solvents DMF (20 mL) and MeOH (20 mL) were added to the solid and the mixture was sonicated for 10 min. The bottle was capped and placed into an 80° C. oven for 1 d. The resulting colorless rod-shape crystals (mp>350° C.) were washed with MeOH and air-dried. Yield calculated from the dried sample was 92%. $^1$H NMR (500 MHz, DMSO-$d_6$) δ 13.54 (s, 3H), 8.36 (s, 3H), 8.03 (s, 3H), 7.95 (s, 3H) ppm. $^{19}$F NMR (470 MHz, DMSO-$d_6$) δ−141.5 to −141.6 (m, 6F), −144.7 to −144.9 (m, 6F) ppm. FT-IR: 3469 (m, $v_{N-H}$), 3213 (s, $v_{N=C-H}$), 3147 (s, $v_{N-C-H}$), 2966 (m, $v_{C=C-H}$), 1653 (m, $v_{C=N}$), 1570 (s, $v_{C=C}$), 1491 (s), 1427 (s), 1394 (s), 1342 (m), 1219 (m), 1155 (m), 1025 (s), 980 (s), 962 (s), 949 (m), 804 (s) cm$^{-1}$. Anal. calcd (%) for $C_{33}F_{12}H_{12}N_6$: C, 54.99; H, 1.68; N, 11.66. Found: C, 54.61; H, 1.46; N, 11.56. HRMS (Cl$^+$ mode): Calculated for $C_{33}H_{12}F_{12}N_6$: 720.0932. Found: 720.0926.

References cited herein are incorporated in their entirety: (1) *Metal-Organic Frameworks: Design and Application*, MacGillivray, L. R. (Ed.), Wiley (2010); (2) Feng, X., Ding, X. & Jiang, D. Covalent organic frameworks. *Chem. Soc. Rev.* 41, 6010-6022 (2012); (3) Adrien P. Côté, A. P., Benin, A. I., Ockwig, N. W., O'Keeffe, M., Matzger, A. J. & Yaghi, O. M. Porous, crystalline, covalent organic frameworks. *Science* 310, 1166-1170 (2005); (4) Wade, C. R., Li, M. & Dincă, M. Facile deposition of multicolored electrochromic MOF thin films. *Angew. Chem. Int. Ed.* 52, 13377-13381 (2013); (5) Colson, W. J. et al. Oriented 2D covalent organic framework thin films on single-layer graphene. *Science* 332, 228-231 (2011); (6) Aoyama, Y. Functional organic zeolite analogues. *Top. Curr. Chem.* 198, 131-161 (1998); (7) He, Y.; Xiang, S. & Chen, B. A microporous hydrogen-bonded organic framework for highly selective $C_2H_2/C_2H_4$ separation at ambient temperature. *J. Am. Chem. Soc.* 133, 14570-14573 (2011); (8) Li, P. et al. A homochiral microporous hydrogen-bonded organic framework for highly enantioselective separation of secondary alcohols. *J. Am. Chem. Soc.*

136, 547-549 (2014); (9) Jones, J. T. A. et al. Modular and predictable assembly of porous organic molecular crystals. *Nature* 474, 367-371 (2011); (10) Zhang, G. & Mastalerz, M. Organic cage compounds—from shape-persistency to function. *Chem. Soc. Rev.* 43, 1934-1947 (2014); (11) Mastalerz, M. & Oppel, I. M. Rational construction of an extrinsic porous molecular crystal with an extraordinary high specific surface area. *Angew. Chem. Int. Ed.* 51, 5252-5255 (2012); (12) Cooper, A. I. Molecular organic crystals: from barely porous to really porous. *Angew. Chem. Int. Ed.* 51, 7892-7894 (2012); (13) Schneider, M. W. et al. Periphery-substituted [4+6] salicylbisimine cage compounds with exceptionally high surface areas: influence of the molecular structure on nitrogen sorption properties. *Chem. Eur. J.* 18, 836-847 (2012); (14) Mastalerz, M., Schneider, M. W., Oppel, I. M. & Presly, O. et al. A salicylbisimine cage compound with high surface area and selective $CO_2/CH_4$ adsorption. *Angew. Chem. Int. Ed.* 50, 1046-1051 (2011); (15) Zhang, G., Presly, O., White, F., Oppel, I. M. & Mastalerz, M. A Shape-Persistent Quadruply Interlocked Giant Cage Catenane with Two Distinct Pores in the Solid State. *Angew. Chem. Int. Ed.* 53, early view (2014); (16) Zhang, G., Presly, O., White, F., Oppel, I. M. & Mastalerz, M. A permanent mesoporous organic cage with an exceptionally high surface area. *Angew. Chem. Int. Ed.* 53, 1516-1520 (2014); (17) Luo, X.-Z. et al. A microporous hydrogen-bonded organic framework: exceptional stability and highly selective adsorption of gas and liquid. *J. Am. Chem. Soc.* 135, 11684-11687 (2013); (18) Yang, W. et al. Exceptional thermal stability in a supramolecular organic framework: porosity and gas storage. *J. Am. Chem. Soc.* 132, 14457-14469 (2010); (19) Brunet, P., Simard, M. & Wuest, J. D. Molecular tectonics. Porous hydrogen-bonded networks with unprecedented structural integrity. *J. Am. Chem. Soc.* 119, 2727-2738 (1997); (20) Meyer, E. A., Castellano, R. K. & Diederich, F. Interactions with aromatic rings in chemical and biological recognition. *Angew. Chem. Int. Ed.* 42, 1210-1250 (2003); (21) Deshpande, R. K., Minnaar, J. L. & Telfer, S. G. Thermolabile groups in metal-organic frameworks: Suppression of network interpenetration, post-synthetic cavity expansion, and protection of reactive functional groups. *Angew. Chem. Int. Ed.* 49, 4598-4602 (2010); (22) Procopio, E. Q., Padial, N. M., Masciocchi, N., Galli, S., Oltra, J. E., Barea, E. & Navarro, J. A. R. A highly porous interpenetrated MOF-5-type network based on bipyrazolate linkers. *Cryst Eng Comm* 15, 9352-9355 (2013); (23) Padial, N. M. et al. Highly Hydrophobic Isoreticular Porous Metal-Organic Frameworks for the Capture of Harmful Volatile Organic Compounds. *Angew. Chem. Int. Ed.* 52, 8290-8294 (2013); (24) Kingston, D. G. I., Hobrock, B. W., Bursey, M. M. & Bursey, J. T. Intramolecular hydrogen transfer in mass spectra. III. Rearrangements involving the loss of small neutral molecules. *Chem. Rev.* 75, 693-730 (1975); (25) Nguyen, J. G. & Cohen, S. M. Moisture-resistant and superhydrophobic metal-organic frameworks obtained via postsynthetic modification. *J. Am. Chem. Soc.* 132, 4560-4561 (2010); (26) Chen, T.-H., Popov, I., Zenasni, O., Daugulis, O. & Miljanić, O. Š. Superhydrophobic perfluorinated metal-organic frameworks. *Chem. Commun.* 49, 6846-6848 (2013); (27) Yang, C. et al. Fluorous metal-organic frameworks with superior adsorption and hydrophobic properties toward oil spill cleanup and hydrocarbon storage. *J. Am. Chem. Soc.* 133, 18094-18097 (2011); (28) Yang, C., Wang, X. & Omary, M. A. Fluorous metal-organic frameworks for high-density gas adsorption. *J. Am. Chem. Soc.* 129, 15454-15455 (2007); (29) Atwood, J. L., Barbour, L. J. & Jerga, A. Storage of methane and Freon by interstitial van der Waals confinement. *Science* 296, 2367-2369 (2002); (30) IPCC Fourth Assessment Report, Climate Change 2007: Net Global Radiative Forcing, Global Warming Potentials and Patterns of Forcing; (31) Eddaoudi, M., Kim, J., Rosi, N., Vodak, D., Wachter, J., O'Keeffe, M. & Yaghi, O. M. Systematic design of pore size and functionality in isoreticular MOFs and their application in methane storage. *Science* 295, 469-472 (2002); and (32) Tanabe, K. K. & Cohen, S. M. Postsynthetic modification of metal-organic frameworks—a progress report. *Chem. Soc. Rev.* 40, 498-519 (2011).

The disclosure herein, in one embodiment, provides a method of synthesizing a highly fluorinated trispyrazole 1, which assembles into a porous organic structure held together by a robust combination of hydrogen bonding and [π . . . π] stacking. This assembled material is an example of an nCOF, and is: lightweight, thermally and hydrolytically stable, and is highly adsorbent for hydrocarbons and their halogenated derivatives, many of which are potent greenhouse gases. Further, in some embodiments, such compounds as disclosed herein are thus suitable for separation of Xylene Isomers and other hydrocarbons, fluorocarbons, and freons, and may further be useful in adsorbing components of oil found in oil spills.

What is claimed is:

1. A non-covalent organic framework comprising a compound of:

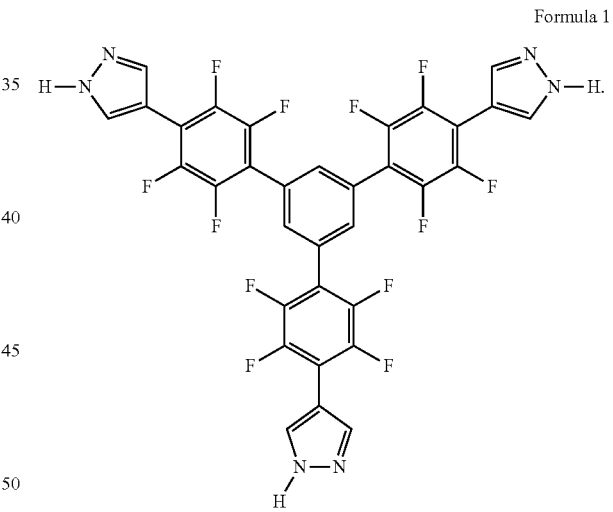

Formula 1

2. The non-covalent organic framework of claim 1, wherein said compound of Formula 1 comprises at least one polymorph.

3. The non-covalent organic framework of claim 1, wherein said compound of Formula 1 comprises a mixture of polymorphs.

4. A compound of Formula 1, wherein said compound forms a porous supramolecular structure.

5. The non-covalent framework of claim 1, wherein said framework is comprised of the compound of Formula 1, wherein said compound comprises a unit cell comprising coordinates of Table 2.

6. The non-covalent organic framework of claim 1, wherein said framework comprises fluorine lined channels, wherein said channels are about 16.5 Angstroms in diameter.

7. The non-covalent organic framework of claim 1, wherein said framework comprises a weight adsorption capacity of about 75% for analytes.

8. The non-covalent organic framework of claim 6, wherein said channels adsorb analytes, wherein said analytes comprise aliphatic hydrocarbons, aromatic hydrocarbons, fluorocarbons; and freons.

9. The non-covalent organic framework of claim 1, wherein the framework differentially binds ortho-xylene; meta-xylene and para-xylene.

10. The non-covalent organic framework of claim 9, wherein the framework differentially binds ortho-xylene by at least 20 weight %.

11. The non-covalent organic framework of claim 9, wherein the framework differentially binds meta-xylene by at least 20 weight %.

12. The non-covalent organic framework of claim 9, wherein the framework differentially binds para-xylene at less than 10 weight %.

13. The non-covalent organic framework of claim 1, wherein the framework is thermally stable, hydrolytically stable, or both.

14. The non-covalent organic framework of claim 1, wherein the framework adsorbs $N_2$, $O_2$ and $CO_2$.

15. A non-covalent organic framework comprising a compound wherein the compound comprises:
a central ring, wherein the central ring is selected from a group comprising: 1,2,3,4,5,6-hexasubstituted benzene; a 1,2,4,5-tetrasubstituted benzene; a 1,3,5-trisubstituted or a 1,4-disubstituted benzene; wherein any of positions 1, 2, 3, 4, 5, and 6 may be substituted or unsubstituted, wherein when said groups are substituted they comprise alternating electron poor and electron rich groups or rings, wherein said electron-poor groups or rings comprise tetra, tri or di fluorobenzenes, oligocyanobenzenes, and wherein an electron-rich group of ring comprises benzene, pirydone, triazole, pyrazole, pyridine, and substituted benzenes.

* * * * *